United States Patent [19]

Sato et al.

[11] Patent Number: 4,791,209

[45] Date of Patent: Dec. 13, 1988

[54] FUROBENZISOXAZOLE DERIVATIVES

[75] Inventors: Haruhiko Sato, Tokyo; Hiroshi Koga, Saitama; Takashi Dan; Etsuro Onuma, both of Tokyo, all of Japan

[73] Assignee: Chugai Seiyako Kabushiki Kaisha, Tokyo, Japan

[21] Appl. No.: 860,210

[22] Filed: May 6, 1986

[30] Foreign Application Priority Data

May 22, 1985 [JP] Japan ................... 60-109729
Dec. 23, 1985 [JP] Japan ................... 60-290133

[51] Int. Cl.$^4$ .................. C07D 498/04; A61K 31/42
[52] U.S. Cl. ...................... 548/242; 548/241; 549/60; 549/467; 549/468; 514/379
[58] Field of Search ............... 548/241, 242; 514/379

[56] References Cited

U.S. PATENT DOCUMENTS 4,456,612  6/1984  Plattner et al. ............ 548/242
4,490,384 12/1984  Plattner et al. ............ 548/241
4,732,906  3/1988  Koga et al. .

FOREIGN PATENT DOCUMENTS 0119294  9/1984  European Pat. Off. .
0126342 11/1984  European Pat. Off. .

OTHER PUBLICATIONS

Plattner et al, "Substitutes 5,6-Dihydrofuro[3,2-f]-1,-2-Benzisoxazole-6-Carboxylic Acids: High-Ceiling Diuretics with Uricosuric Activity", *J. Med. Chem.*, 1984, 27, pp. 1016 to 1026.

Gregary M. Shutske et al., J. Med. Chem., 25, 36-44 (1982).

*Primary Examiner*—Donald G. Daus
*Assistant Examiner*—E. Bernhardt
*Attorney, Agent, or Firm*—Browdy and Neimark

[57] ABSTRACT

Novel furobenzisoxazole derivatives of the formula (I):

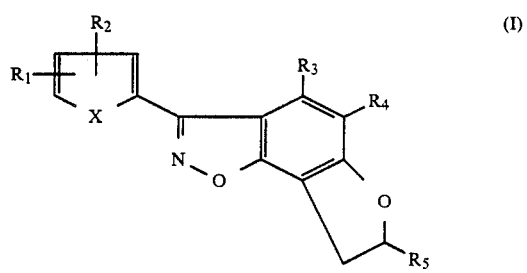

(wherein $R_1$, $R_2$, $R_3$ and $R_4$ which may be the same or different represent a hydrogen atom, a halogen atom, or a lower alkyl group having 1-4 carbon atoms; $R_5$ is a hydroxymethyl group, a carboxyl group or a lower alkoxy carbonyl group having 1-3 carbon atoms; and X is a sulfur atom or a —CH=CH— group), as well as intoxic salts thereof when $R_5$ is a carboxyl group, and process for preparing the same are disclosed.

The derivatives of formula (I) and nontoxic salts thereof have hypotensive, uricosuric and diuretic activities and hence ae useful as therapeutics for treating hyperuricemia, edema and hypertension.

2 Claims, No Drawings

FUROBENZISOXAZOLE DERIVATIVES

The present invention relates to novel furobenzisoxazole derivatives of the formula (I):

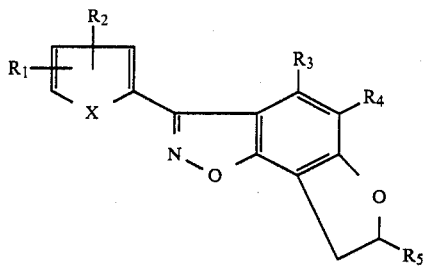

(wherein $R_1$, $R_2$, $R_3$ and $R_4$ which may be the same or different represent a hydrogen atom, a halogen atom, or a lower alkyl group having 1–4 carbon atoms; $R_5$ is a hydroxymethyl group, a carboxyl group or a lower alkoxy carbonyl group having 1–3 carbon atoms; and X is a sulfur atom or a —CH=CH— group), as well as intoxic salts thereof when $R_5$ is a carboxyl group.

The derivatives of formula (I) and intoxic salts thereof have hypotensive, uricosuric and diuretic activities and hence are useful as therapeutics for treating hyperuricemia, edema and hypertension.

Compounds are known which have both uricosuric and diuretic activities as do the compounds of the present invention and they are phenoxyacetic acids typified by thienyllic acid (U.S. Pat. No. 3,758,506).

Diuretics known to have uricosuric activity like the compounds of the present invention are phenoxyacetic acids typified by thienylic acid (U.S. Pat. No. 3,758,506).

Conventional diuretic hypotensive agents are extensively used as drugs of the first choice in the treatment of hypertension, but they have a high potential of causing hyperuricemia as a side effect. Furthermore, hypertension is often complicated by hyperuricemia and many cases of hyperuricemia are belived to be caused by disorders in the excretion of uric acid. Under these circumstances, there exists a strong need in medical fields for the development of diuretics having uricosuric activity. As already mentioned, thienylic acid is known to be a potential diuretic having uricosuric activity, but the sale or the development of the compound has been suspended in most countries because of the high possibility of causing liver disorders as a side effect.

As a result of concerted efforts made to overcome these disadvantages, the present inventors have found that the furobenzisoxazole derivatives of formula (I) have both uricosuric and diuretic activities and yet cause minimum side effects on the liver. The present invention has been accomplished on the basis of this finding.

In the compounds of formula (I), the halogen atom may be illustrated by a chlorine, bromine or fluorine atom, and the lower alkyl group may be a straight- or branched-chained alkyl group having 1 to 4 carbon atoms. When $R_5$ is a carboxyl group, the compounds of the present invention may form salts with bases. The salts should be pharmaceutically acceptable ones such as those illustrated by alkali metal salts, alkaline earth metal salts, amine salts and substituted amine salts. More specific examples of such salts are sodium salts, potassium salts, calcium salts, magnesium salts, ammonium salts, lower alkyl amine salts and ethanolamine salts.

The furobenzisoxazole derivatives of formula (I) in accordance with the present invention are novel and may be prepared by a process which comprises first causing a base to act on compounds of formula (II) in an inert solvent, and by then optionally subjecting the reaction product to hydrolysis in a conventional manner:

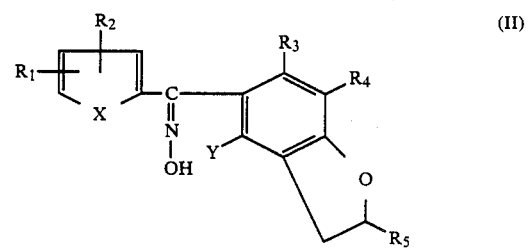

(wherein $R_1$ to $R_5$ and X are the same as defined in formula (I); Y is a halogen atom).

Examples of the inert solvent that may be used in preparing the compound (I) from the compound (II) include water, ethers, alcohols, hydrocarbons, and aromatic hydrocarbons, and aprotic polar solvents such as N,N-dimethylformamide and dimethyl sulfoxide. Usable bases are hydrides, alkoxides and hydroxides of alkali metals such as sodium and potassium. The reaction temperature may be properly selected from the range of 0°–150° C.

Compounds of formula (I) in accordance with the present invention include those represented by formula (Ia) wherein $R_5$ in formula (I) is a hydroxymethyl group. These compounds may be prepared by causing peracids to act on compounds of formula (III). If desired, the compounds of formula (Ia) may be oxidized with oxidizing agents to give compounds (Ib) wherein $R_5$ in formula (I) is a carboxyl group and which are also included within the scope of the compounds of formula (I):

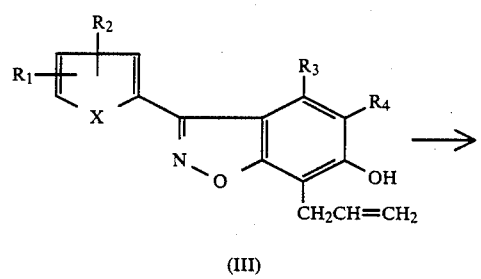

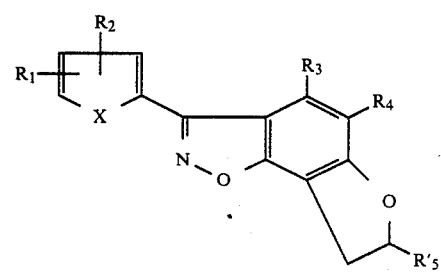

(Ia): $R'_5$ = —CH₂OH
(Ib): $R'_5$ = —COOH

[wherein $R_1$, $R_2$, $R_3$, $R_4$ and X are the same as defined in formula (I)].

Examples of the peracid that can be used in the reaction for preparing the compounds of formula (Ia) include m-chloroperbenzoic acid, perbenzoic acid and peracetic acid. Suitable oxidizing agents are oxides of metals such as chromium and manganese. The temperature and solvent that may be employed in the reaction for preparing the compounds of formula (Ia) or (Ib) are the same as those illustrated in connection with the raction for converting the compounds (II) to (I).

The compounds (I) of the present invention wehrein $R_5$ is a lower alkoxy carbonyl group may be prepared by esterifying the compounds (Ib) wherein $R_5$ is a carboxyl group in accordance with a routine method.

The diuretic and uricosuric activities of the compounds of the present invention were confirmed by the following experiment.

Method

Seven-week old Wistar-Imamichi rats that had been starved for 24 hours were divided in groups of four or five heads so that the animals of each group would excrete almost the same amount of urine. After forced urination, the rats were orally administered the test compounds that were suspended in physiological saline containing 3% gum arabic in a dose volume of 25 ml per kg of the body weight. The compounds of the present invention were administered typically in an amount of 100 mg/kg. Control rats were given only physiological saline containing 3% gum arabic. The animals were housed in separate metabolic cages and the urine excreted from each animal was collected over a period of 6 hours or 24 hours following the administration of the test compounds or physiological saline after complete starvation. The urine volume was directly read on a measuring cylinder after forced urination thereinto, and the amount of urine per kg of the body weight was calculated. The amount of uric acid excreted in the urine was determined by the uricase-catalase method.

Results

As is apparent from the following table, the compounds of the present invention exhibited significant levels of diuretic and uricosuric activities, which were found to be long-lasting and dose-dependent. The compound numbers given in the table are keyed to the specific Examples shown later in this specification.

(500 ml), m-chloroperbenzoic acid (20.8 g) was added in small portions under agitation, and the mixture was refluxed for 4 hours. After cooling the mixture, water and an aqueous solution of 2N sodium hydroxide (80 ml) were added and the mixture was subjected to extraction with methylene chloride. The methylene chloride layer was washed with water and dried. By distilling off the solvent, 18 g of 7,8-dihydro-3-phenylfuro[2,3-g]-1,2-benzisoxazole-7-methanol was obtained. m.p. 107°–109° C. This compound exhibited a mass spectrum having a molecular ion peak at m/e 267.

EXAMPLE 2

A portion (5.5 g) of the 7,8-dihydro-3-phenylfuro[2,3-g]-1,2-benzisoxazole-7-methanol prepared in Example 1 was dissolved in 200 ml of acetone. To the stirred solution, a mixture of chromium (VI) oxide (10 g), water (20 ml) and concentrated sulfuric acid (16 g) was added dropwise over time, and the solution was left to stand overnight. The insolubles were filtered off by suction. After distilling off the acetone, water was added to the residue and the mixture was subjected to extraction with ethyl acetate. The ethyl acetate layer was washed with water and dried, followed by distilling off the solvent. The residue was recrystallized with acetonitrile to yield 2.5 g of 7,8-dihydro-3-phenylfuro[2,3-g]-1,2-benzisoxazole-7-carboxlic acid. m.p. 219°–220° C. This compound exhibited a mass spectrum having a molecular ion peak at m/e 281.

EXAMPLE 3

A portion (10 g) of the 7,8-dihydro-3-phenylfuro[2,3-g]-1,2-benzisoxazole-7-methanol prepared in Example 1 was dissolved in 300 ml of methylene chloride. To the ice-cooled solution, sulfuryl chloride (9 g) was added over time under agitation. The mixture was thereafter stirred for 8 hours at room temperature. The solvent was distilled off and the resulting residue was purified by column chromatography using methylene chloride as an eluant, whereupon 3.3 g of 5-chloro-7,8-dihydro-3-phenylfuro[2,3-g]-1,2benzisoxazole-7-methanol was obtained. This compound (3.3 g) was dissolved in 100 ml of acetone and, to the stirred solution, a mixture of chromium (VI) oxide (4 g), water (6 ml) and concentrated sulfuric acid (5.9 g) was added dropwise over time, and the solution was stirred for 2.5 hours at room temperature. The insolubles were filtered off by suction. After distilling off the acetone, water was added to the

TABLE

| | Amount of urine | | | | Uric acid excretion | | | |
| --- | --- | --- | --- | --- | --- | --- | --- | --- |
| | 0–6 hours | | 0–24 hours | | 0–6 hours | | 0–24 hours | |
| Test compound | (ml/kg) | (%) | (ml/kg) | (%) | (mg/kg) | (%) | (mg/kg) | (%) |
| Control group | 20.0 ± 0.8 | 100 | 36.9 ± 1.1 | 100 | 3.23 ± 0.09 | 100 | 10.95 ± 0.36 | 100 |
| Compound 3 | 22.8 ± 1.1 | 113.8[a] | 39.2 ± 1.1 | 106.3 | 4.52 ± 0.12 | 139.8[c] | 13.30 ± 0.71 | 121.4[b] |
| Control group | 15.8 ± 1.9 | 100 | 34.0 ± 2.8 | 100 | 3.23 ± 0.15 | 100 | 11.63 ± 0.83 | 100 |
| Compound 5 | 24.1 ± 3.9 | 152.6 | 39.7 ± 3.7 | 116.8 | 3.85 ± 0.20 | 119.0[a] | 13.76 ± 0.76 | 118.3 |
| Control group | 18.5 ± 1.2 | 100 | 33.1 ± 2.1 | 100 | 3.74 ± 0.15 | 100 | 11.52 ± 0.42 | 100 |
| Compound 16 | 27.7 ± 2.2 | 149.3[b] | 43.9 ± 2.4 | 132.5[b] | 4.94 ± 0.20 | 132.0[b] | 13.23 ± 1.85 | 114.8 |
| Control group | 16.3 ± 1.1 | 100 | 32.3 ± 1.0 | 100 | 3.61 ± 0.16 | 100 | 11.11 ± 0.60 | 100 |
| Compound 21 | 20.5 ± 3.0 | 125.3 | 39.6 ± 1.9 | 122.5[a] | 4.14 ± 0.43 | 114.8 | 15.20 ± 1.01 | 136.8[b] | a: $p < 0.05$, b: $p < 0.01$, c: $p < 0.001$

The following examples are provided for further illustrating the claimed compunds but are not to be construed as limiting the invention.

EXAMPLE 1

To an ice-cooled solution of 7-allyl-6-hydroxy-3-phenyl-1,2-benzisoxazole (17.5 g) in methylene chloride residue and the mixture was subjected to extraction with ether. The ether layer was washed with water and dried, followed by distilling off of the solvent. The residue was recrystallized with acetonitrile to yield 1 g of 5-chloro-7,8-dihydro-3-phenylfuro[2,3-g]-1,2-benzisoxazole-7-carboxylic acid. m.p. 221°–224° C. This compound exhibited a mass spectrum having a molecular ion peak at m/e 315.

EXAMPLE 4

A mixture of 7.2 g of the 7,8-dihydro-3-phenylfuro[2,3-g]-1,2-benzisoxazole-7-methanol prepared in Example 1, 35 ml of acetic anhydride and 160 ml of benzene was refluxed for 5 hours. After distilling off the solvent under vacuum, the residue was dissolved in 200 ml of methylene chloride, and 4.8 g of bromine was slowly added to the stirred solution. After continuing the agitation for 10 hours at room temprature, the solvent was distilled off. The residue was purified by column chromatography using methylene chloride as an eluant, whereupon 1.6 g of 7-acetoxymethyl-5-bromo-7,8-dihydro-3-phenylfuro[2,3-g]-1,2-benzisoxazole was obtained. A portion (1.5 g) of this compound was mixed with 30 ml of ethanol and 10 ml of an aqueous solution of 2N sodium hydroxide and the mixture was refluxed for 10 minutes. After cooling, the mixture was rendered acidic by addition of 15 ml of 2N HCl. Water was added to the mixture and the resulting crystal was recovered by filtration. By washing the crystal with water, 0.9 g of 5-bromo-7,8-dihydro-3-phenylfuro[2,3-g]-1,2-benzisoxazole-7-methanol was obtained. m.p. 164°–165.5° C. This compound exhibited a mass spectrum having a molecular ion peak at m/e 345 and 347.

EXAMPLE 5

A portion (0.7 g) of the 5-bromo-7,8-dihydro-3-phenylfuro[2,3-g]-1,2-benzisoxazole-7-methanol prepared in Example 4 was dissolved in 50 ml of acetone. To the stirred solution, a mixture of chromium (VI) oxide (1 g), water (3 ml) and concentrated sulfuric acid (1.4 g) was added dropwise over time, and the solution was stirred for 6 hours at room temperature. The insolubles were filtered off by suction. After distilling off the acetone, water was added to the residue and the mixture was subjected to extraction with ether. The ether layer was washed with water and dried. After distilling off the solvent, the residue was recrystallized with acetone-water, yielding 0.4 g of 5-bromo-7,8-dihydro-3-phenylfuro[2,3-g]-1,2-benzisoxazole-7-carboxylic acid. m.p. 241.5°–243.5° C. (with decomposition).

Elemental analysis:

Calcd. for $C_{16}H_{10}BrNO_4$ (%): C 53.36, H 2.80, N 3.89; Found (%): C 53.66, H 2.89, N 3.73.

EXAMPLE 6

A mixture of 5-benzoyl-4,7-dichloro-2,3-dihydrobenzo[b]furan-2-carboxylic acid (2.5 g), hydroxylamine hydrochloride (5.2 g) and pyridine (50 ml) was stirred for 18 hours at 90°–100° C. After cooling, the mixture was rendered acidic with HCl and subjected to extraction with ether. Ether was distilled off and the residual water was removed by azeotropic distillation with benzene, yielding 2.6 g of 4,7-dichloro-2,4-dihydro-5-(α-hydroxyiminobenzyl)benzo[b]furan-2-carboxylic acid. This compound (2.6 g) was dissolved in 20 ml of anhydrous dimethylformamide, and to the ice-cooled solution, 0.9 g of 60% sodium hydride was added in small portions under stirring. After continuing the agitation for 7 hours at room temperature, the mixture was left to stand overnight. After addition of water, the mixture was rendered acidic with HCl and subjected to extraction with ether. The ether layer was washed with water and dried. After distilling off the solvent, the residue was recrystallized with acetonitrile-benzene, yielding 0.9 g of 5-chloro-7,8-dihydro-3-phenylfuro[2,3-g]-1,2-benzisoxazole-7-carboxylic acid. The physical data of this compound were in agreement with those of the product obtained in Example 3.

EXAMPLE 7

Four grams of 4,7-dichloro-2,3-dihydro-5-(2-methylbenzoyl)benzo[b]furan-2-carboxylic acid was treated as in Example 6 to obtain 1 g of 5-chloro-7,8-dihydro-3-(2-methylphenyl)furo[2,3-g]-1,2-benzisoxazole-7-carboxylic acid. m.p. 192°–195° C. (recrystallized from acetonitrile-water). This compound exhibited a mass spectrum having a molecular ion peak at m/e 329.

EXAMPLE 8

Using 1.6 g of 4,7-dichloro-2,3-dihydro-5-(2-thenoyl)-benzo[b]-furan-2-carboxylic acid as the starting material, the procedures described in Example 6 were repeated to provide 0.4 g of 5-chloro-7,8-dihydro-3-(2-thienyl)furo[2,3-g]-1,2-benzisoxazole-7-carboxylic acid. m.p. 249°–251° C. (with decomposition; recrystallized from acetone-water). This compound exhibited a mass spectrum having a molecular ion peak at m/e 321.

EXAMPLE 9

To the ice-cooled solution of 7-allyl-6-hydroxy-5-methyl-3-phenyl-1,2-benzisoxazole (4.5 g) in methylene chloride (200 ml), 7.6 g of m-chloroperbenzoic acid was added in small portions under agitation, and the solution was subsequently refluxed for 3 hours. After cooling the solution, water and 50 ml of an aqueous solution of 2N sodium hydroxide were added, and the mixture was subjected to extraction with methylene chloride. The methylene chloride layer was washed with water and dried. By distilling off the solvent, 4.6 g of 7,8-dihydro-5-methyl3-phenylfuro[2,3-g]-1,2-benzisoxazole-7-methanol was obtained. m.p. 130°–133° C. This compound exhibited a mass spectrum having a molecular ion peak at m/e 281.

EXAMPLE 10

A portion (4.5 g) of the 7,8-dihydro-5-methyl-3-phenylfuro[2,3-g]-1,2-benzisoxazole-7-methanol prepared in Example 9 was dissolved in 150 ml of acetone. To the stirred solution, a mixture of chromium (VI) oxide (5.9 g), water (12 ml) and concentrated sulfuric acid (8.3 g) was added dropwise over time, and the resulting mixture was stirred for 2 hours at room temperature. After leaving the mixture to stand overnight, the insolubles were filtered off by suction. After distilling off the acetone, water was added and the mixture was subjected to extraction with ether. The ether layer was washed with water and dried. After distilling off the solvent, the residue was recrystallized from acetone-water to yield 2.9 g of 7,8-dihydro-5-methyl-3-phenylfuro[2,3-g]-1,2-benzisoxazole-7carboxylic acid. m.p. 210°–213° C. This compound exhibited a mass spectrum haivng a molecular ion peak at m/e 295.

EXAMPLE 11

To the ice-cooled solution of 7-allyl-5-chloro-3-(2-fluorophenyl)-6-hydroxy-1,2-benzisoxazole (9.5 g) in methylene chloride (200 ml), m-chloroperbenzoic acid (16.4 g) was added in small portions under agitaiton, and the solution was subsequently refluxed for 3 hours. After cooling the solution, water and 100 ml of an aqueous solution of 2N sodium hydroxide were added and the mixture was subjected to extraction with methylene chloride. The methylene chloride layer was washed with water and dried. By distilling off the solvent, 6.5 g of 5-chloro-7,8-dihydro-3-(2-fluorophenyl)furo[2,3-g]-1,2-benzisoxazole-7-methanol was obtained. m.p. 136°–139° C. This compound exhibited a mass spectrum having a molecular ion peak at m/e 319.

EXAMPLE 12

A portion (6.4 g) of the 5-chloro-7,8-dihydro-3-(2-fluorophenyl)furo[2,3-g]-1,2-benzisoxazole-7-methanol prepared in Example 11 was dissolved in 150 ml of acetone. To the stirred solution, a mixture of chromium (VI) oxide (7.2 g), water (15 ml) and concentrated sulfuric acid (10.2 g) was added dropwise overtime, and the mixture was agitated for 8 hours at room temperature. The insolubles were filtered off by suction. After distilling off the acetone, water was added and the mixture was subjected to extraction with ether. The ether layer was washed with water and dried. After distilling off the solvent, the residue was recrystallized from acetone-water, yielding 6.0 g of 5-chloro-7,8-dihydro-3-(2-fluorophenyl)furo[2,3-g]-1,2-benzisoxazole-7-carboxylic acid. m.p. 199°–200° C. This compound exhibited a mass spectrum having a molecular ion peak at m/e 333.

Elemental analysis: Calcd for (%): $C_{16}H_9ClFNO_4$ (%): 57.59, H 2.72, N 4.20; Found (%): C 57.50, H 2.77, N 4.40.

EXAMPLE 13

To the ice-cooled solution of 7-allyl-5-chloro-3-(2-chlorophenyl)-6-hydroxy-1,2-benzisoxazole (4.5 g) in methylene chloride (200 ml), 6.6 g of m-chloroperbenzoic acid was added in small portions under agitation, and the mixture was subsequently refluxed for 4 hours. After cooling the mixture, water and 50 ml of an aqueous solution of 2N sodium hydroxide were added and the mixture was extracted with methylene chloride. The methylene chloride layer was washed with water and dried. By distilling off the solvent, 4.6 g of 5-chloro-3-(2-chlorophenyl)-7,8-dihydrofuro[2,3-g]-1,2-benzisoxazole-7-methanol was obtained. m.p. 162°–163° C. This compound exhibited a mass spectrum having a molecular ion peak at m/e 335.

EXAMPLE 14

A portion (4.5 g) of the 5-chloro-3-(2-chlorophenyl)7,8-dihydrofuro[2,3-g]-1,2-benzisoxazole-7-methanol prepared in Example 13 was dissolved in 200 ml of acetone. To the stirred solution, a mixture of chromium (VI) oxide (4.9 g), water (10 ml) and concentrated sulfuric acid (6.9 g) was added dropwise over time, and the resulting mixture was stirred for 8 hours at room temperature. The insolubles were filtered off by suction. After distilling off the acetone, water was added to the residue and the solution was subjected to extraction with ether. The ether layer was washed with water and dried. After distilling off the solvent, the residue was recrystallized from acetone-water, yielding 2.6 g of 5-chloro-3-(2-chlorophenyl)-7,8-dihydrofuro[2,3-g]-1,2-benzisoxazole-7-carboxylic acid. m.p. 220°–221.5° C. This compound exhibited a mass spectrum having a molecular ion peak at m/e 349.

Elemental analysis:
Calcd. for (%): $C_{16}H_9Cl_2NO_4$ (%): C 54.88, H 2.59, N 4.00; Found (%): C 54.86, H 2.66, N 4.01.

EXAMPLE 15

A mixture of 4,7-dichloro-2,3-dihydro-5-(4-fluorobenzoyl)benzo[b]furan-2-carboxylic acid (12.4 g), hydroxylamine hydrochloride (20.6 g) and pyridine (120 ml) was refluxed for 5.5 hours. Aftre distilling off the solvent, water was added to the mixture, which then was rendered acidic with HCl and subjected to extraction with ether. The ether layer was washed with water and dried. By distilling off the solvent, 12.8 g of 4,7-dichloro-2,3-dihydro-5-(4-fluoro-α-hydroxyiminobenzyl)benzo[b]furan-2-carboxylic acid was obtained. This compound (12.8 g) was dissolved in 150 ml of anhydrous dimethylformamide, and to the ice-cooled solution, 4.8 g of 60% sodium hydride was added in small portions under agitation. After continuing the agitation for 5 hours at room temperature, the mixture was left to stand overnight. Water was added to the mixture, which then was rendered acidic with HCl and subjected to extraction with ether. The ether layer was washed with water and dried. After distilling off the solvent, the residue was recrystallized from acetone-water, yielding 4.4 g of 5-chloro-7,8-dihydro-3-(4-fluorophenyl)-furo[2,3-g]-1,2-benzisoxazole-7-carboxylic acid. m.p. 215°–218° C. This compound exhibited a mass spectrum having a molecular ion peak at m/e 333.

Elemental analysis:
Calcd. for (%): $C_{16}H_9ClFNO_4$ (%): C 57.59, H 2.72, N 4.20;
Found (%): C 57.53, H 2.79, N 4.04.

EXAMPLE 16

A mixture of 4,7-dichloro-2,3-dihydro-5-(3-fluorobenzoyl)benzo[b]furan-2-carboxylic acid (12.2 g), hydroxylamine hydrochloride (24.4 g) and pyridine (120 ml) was refluxed for 10 hours. After distilling off the solvent, water was added to the mixture, which then was rendered acidic with HCl and subjected to extraction with ether. The ether layer was washed with water and dried. By distilling off the solvent, 13.5 g of 4,7-dichloro-2,3-dihydro-5-(3-fluoro-u-hydroxyiminobenzyl)benzo[b]furan-2-carboxylic acid was obtained. This compound (13.5 g) was dissolved in anhydrous dimethylformamide (140 ml), and to the ice-cooled solution, 4.4 g of 60% sodium hydride was added in small portions under agitation. After continuing the agitation for 8 hours at room temperature, water was added to the mixture which then was rendered acidic with HCl and subjected to exraction with ether. The ether layer was washed with water and dried. After distilling off the solvent, the residue was recrystallized from acetone-water, yielding 2.3 g of 5-chloro-7,8-dihydro-3-(3-fluorophenyl)furo[2,3-g]-1,2-benzisoxazole-7-carboxylic acid. m.p. 209.0°–210.0° C. This compound exhibited a mass spectrum having a molecular ion peak at m/e 333.

Elemental analysis: Calcd. for (%): $C_{16}H_9ClFNO_4$ (%): C 57.59, H 2.72, N 4.20; Found (%): C 57.48, H 2.75, N 4.00

EXAMPLE 17

A mixture of 5-(4-chlorobenzoyl)-4,7-dichloro-2,3-dihydrobenzo[b]furan-2-carboxylic acid (10.8 g), hydroxylamine hydrochloride (20.7 g) and pyridine (100 ml) was refluxed for 13 hours. After distilling off the solvent, water was added to the mixture which then was rendered acidic with HCl and subjected to extraction with ether. The ether layer was washed with water and dried. By distilling off the solvent, 11.0 g of 5-(4-chloro-α-hydroxyiminobenzyl)4,7-dichloro-2,3-dihydrobenzo[b]furan-2-carboxylic acid was obtained. This compound (11 g) was dissolved in anhydrous dimethylformamide (140 ml), and to the ice-cooled solution, 4.0 g of 60% sodium hydride was added in small portions under agitation. After continuing the agitation for 5 hours at room temperature, the mixture was left to stand overnight. Water was added to the mixture, which then was rendered acidic with HCl and subjected to extraction with ether. The ether layer was washed with water and dried. After distilling off the solvent, the residue was recrystallized from acetone-water, yielding 6.5 g of 5-chloro-3-(4-chlorophenyl)-7,8-dihydrofuro[2,3-g]-1,2-benzisoxazole-7-carboxylic acid. m.p. 240°–243° C. (with decomposition). This compound exhibited a mass spectrum having a molecular ion peak at m/e 349.

Elemental analysis: Calcd. for (%): $C_{16}H_9Cl_2NO_4$ (%): C 54.88, H 2.59, N 4.00; Found (%): C 55.05, H 2.69, N 3.82.

EXAMPLE 18

A mixture of 5-(3-chlorobenzoyl)-4,7-dichloro-2,3-dihydrobenzo[b]furan-2-carboxylic acid (11.5 g), hydroxylamine hydrochloride (21.5 g) and pyridine (110 ml) was refluxed for 14 hours. After distilling off the solvent, water was added to the mixture which then was rendered acidic with HCl and subjected to extraction with ether. The ether layer was washed with water an.d dried. By distilling off the solvent, 12 g of 5-(3-chloro-α-hydroxyiminobenzyl)4,7-dichloro-2,3-dihydrobenzo[b]furan-2-carboxylic acid was obtained. This compound (12 g) was dissolved in anhydrous dimethylformamide (150 ml), and to the ice-cooled solution, 3.9 g of 60% sodium hydride was added in small amounts under agitation. After stirring for 8 hours at room temperature, the mixture was left to stand overnight. After adding water, the mixture was rendered acidic with HCl and subjected to extraction with ether. The ether layer was washed with water and dried. After distilling off the solvent, the residue was recrystallized from acetone-water, yielding 5.6 g of 5-chloro-3-(3-chlorophenyl)-7,8-dihydrofuro[2,3-g]-1,2-benzisoxazole-7-carboxylic acid. m.p. 168°–169° C. This compound exhibited a mass spectrum having a molecular ion peak at m/e 349.

Elemental analysis: Calcd. for (%): $C_{16}H_9Cl_2NO_4$ (%): C 54.88, H 2.59, N 4.00; Found (%): C 54.83, H 2.62, N 3.91.

EXAMPLE 19

Four grams of the 5-chloro-7,8-dihydro-3-phenylfuro[2,3-g]-1,2-benzisoxazole-7-carboxylic acid obtained in Example 3 was mixed with concentrated sufluric acid (2 g) and anhydrous ethanol (50 ml), and the resulting mixture was refluxed for 1 hour. After distilling off the ethanol, water was added to the residue which was subjected to extraction with ether. The ether layer was washed with water and dried. After distilling off the solvent, the residue was recrystallized from ether-hexane, yielding 3.1 g of ethyl 5-chloro-7,8-dihydro-3-phenylfuro[2,3-g]-1,2-benzisoxazole-7-carboxylate. m.p. 123°–125° C. This compound exhibited a mass spectrum having a molecular ion peak at m/e 343.

Elemental analysis: Calcd. for $C_{18}H_{14}ClNO_4$ (%): C 62.89, H 4.11, N 4.07; Found (%): C 62.92, H 4.10, N 4.11.

EXAMPLE 20

To the ice-cooled solution of 7-allyl-5-chloro-3-(2,6-difluorophenyl)-6-hydroxy-1,2-benzisoxazole (3.1 g) in methylene chloride (80 ml), 4.6 g of m-chloroperbenzoic acid was added in small portions under agitation, and the mixture was subsequently refluxed for 5 hours. After cooling the mixture, water and an aqueous solution of 2N sodium hydroxide were added and the mixture was subjected to extraction with methylene chloride. The methylene chloride layer was washed with water and dried. By distilling off the solvent, 2.8 g of 5-chloro-3-(2,6-difluorophenyl)-7,8-dihydrofuro[2,3-g]-1,2-benzisoxazole-7-methanol was obtained. m.p. 166°–169° C. This compound exhibited a mass spectrum having a molecular ion peak at m/e 337.

EXAMPLE 21

To the stirred acetone (50 ml) solution of 2.8 g of the 5-chloro-3-(2,6-difluorophenyl)-7,8-dihydrofuro[2,3-g]1,2-benzisoxazole-7-methanol. prepared in Example 20, a mixture of chromium (VI) oxide (3.0 g), water (7 ml) and concentrated sulfuric acid (4.2 g) was added dropwise over time, and the agitation was continued for 9 hours at room temperature. The insolubles were filtered off by suction and the acetone was distilled off. Water was added to the residue, and the solution was subjected to extraction with ether. The ether layer was washed with water and dried. After distilling off the solvent, the residue was recrystallized from acetone-water, yielding 1.0 g of 5-chloro-3-(2,6-difluorophenyl)-7,8-dihydrofuro[2,3-g]-1,2-benzisoxazole-7-carboxylic acid. m.p. 239.5°–241° C. This compound exhibited a mass spectrum having a molecular ion peak at m/e 351.

Elemental analysis: Calcd. for C (%): $C_{16}H_8ClF_2NO_4$ (%): C 54.64, H 2.29, N 3.98; Found (%): C 54.77, H 2.29, N 3.98.

EXAMPLE 22

A mixture of 4-chloro-3-(2-fluorophenyl)-6-hydroxy-1,2-benzisoxazole (7.7 g), potassium carbonate (7.1 g), allyl bromide (6.0 g) and DMF (100 ml) was stirred at 50°–60° C. for 3 hours. After cooling the mixture, water was added and the mixture was extracted with ether. The ether layer was washed with water and dried, and the solvent was distilled off to obtain 8.8 g of 6-allyloxy-4-chloro-3-(2-fluorophenyl)-1,2-benzisoxazole. This compound (8.8 g) was refluxed in 100 ml of aniline for 3.5 hours. After cooling the mixture, concentrated hydrochloric acid and then water were added and the mixture was extracted with ether. The ether layer was washed with water and dried. After distilling off the solvent, the residue was purified by column chromatography using 1% methanol/methylene chloride as an eluant, and 6.3 g of 7-allyl-4-chloro-3-(2-fluorophenyl)-6-hydroxy-1,2-benzisoxazole (m.p. 211°–212° C.) was obtained. This compound (6.4 g) was dissolved in 300 ml of methylene chloride and 10.2 g of m-chloroperbenzoic acid was slowly added to the solution while it was stirred and cooled, and the stirring was continued for 3 hours. After cooling, water and then 50 ml of a 2N sodium hydroxide aqueous solution were added to the mixture, which was extracted with methylene chloride. The mehtylene chloride layer was washed with water and dried, then the solvent was distilled off to yield 5 g of 4-chloro-7,8-dihydro-3-(2-fluorophenyl)furo[2,3-g]-1,2-benzisoxazole-7-methanol. m.p. 109.5°–111° C. This compound exhibited a mass spectrum having a molecular ion peak at m/e 319.

Elemental analysis: Calcd. for $C_{16}H_{11}ClFNO_3$(%) C 60.11, H 3.47, N 4.38; Found (%): C 59.96, H 3.37, N 4.31.

EXAMPLE 23

A portion (4.3 g) of the 4-chloro-7,8-dihydro-3-(2-fluorophenyl)furo[2,3-g]-1,2-benzisoxazole-7-methanol obtained in Example 22 was dissolved in 120 ml of acetone. To the solution, a mixture of chromium (VI) oxide (6.5 g), water (15 ml) and concentrated sulfuric acid (9.3 g) was added dropwise under stirring. The stirring was continued at room temperature for 2 hours, then the mixture was left to stand overnight. The insolubles were filtered off by suction, and the solvent was distilled off. Water was added to the residue, followed by extraction with ether. The ether layer was washed with water and dried, and the solvent was distilled off. The residue was recrystallized from acetone/water to yield 2.7 g of 4-chloro-7,8-dihydro-3-(2-fluorophenyl)furo[2,3-g]-1,2-benzisoxazole-7-carboxylic acid. m.p. 191°–193° C.

This compound exhibited a mass spectrum having a molecular ion peak at m/e 333.

Elemental analysis: Calcd. for $C_{16}H_9ClFNO_4$ (%): C 57.59, H 2.72, N 4.20; ;l Found (%): C 57.75, H 2.65, N 4.15.

We claim:
1. A compound of the formula:

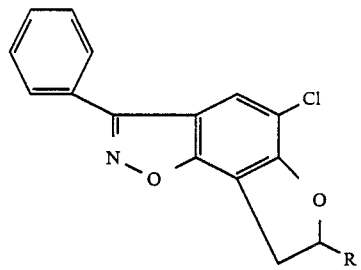

wherein R is a hydroxymethyl group, a carboxyl group or a lower alkoxy carbonyl group having 1 to 3 carbon atoms or an nontoxic salt thereof when R is a carboxyl group.

2. The compound of claim 1, wherein R is a carboxyl group.

* * * * *